United States Patent [19]

Dosako et al.

[11] Patent Number: 5,606,086

[45] Date of Patent: Feb. 25, 1997

[54] IRON LACTOFERRIN COMPLEXES AND PREPARATION THEREOF

[75] Inventors: Shunichi Dosako; Toshio Sakurai; Naomichi Kobayashi, all of Saitama, Japan

[73] Assignee: Snow Brand Milk Products Co., Ltd., Hokkaido, Japan

[21] Appl. No.: 318,778

[22] PCT Filed: Feb. 16, 1994

[86] PCT No.: PCT/JP94/00233

§ 371 Date: Apr. 24, 1995

§ 102(e) Date: Apr. 24, 1995

[87] PCT Pub. No.: WO94/19375

PCT Pub. Date: Sep. 1, 1994

[30] Foreign Application Priority Data

Dec. 16, 1993 [JP] Japan ................................ 5-050061

[51] Int. Cl.$^6$ ................................................ C07F 15/02
[52] U.S. Cl. .......................... 556/138; 556/147; 556/148; 530/394; 530/395; 530/400
[58] Field of Search .................. 556/138, 147, 556/148; 530/400, 394, 395

[56] References Cited

U.S. PATENT DOCUMENTS 4,946,944  8/1990  Frankinet et al. ............... 530/400
5,116,953  5/1992  Dosako et al. .................. 530/400
5,141,743  8/1992  Schryvers ........................ 424/92

*Primary Examiner*—Porfirio Nazario-Gonzalez
*Attorney, Agent, or Firm*—Testa, Hurwitz & Thibeault, LLP

[57] ABSTRACT

Heat resistant carbonate- and/or hydrogencarbonate-iron-Lf complexes in which one molecule of lactoferrin is bound with 15 molecules or over of iron via carbonic acid and/or hydrogencarbonic acid.

Process for the production of above mentioned complexes prepared by adjusting $pH \leq 7$ by adding alkali salts of carbonic acid and/or hydrogencarbonic acid to an aqueous solution containing an iron salt exhibiting $pH \leq 4$ when dissolved in water and lactoferrins, or adding an iron salt and lactoferrin solution to carbonic acid and/or hydrogencarbonic acid solution, or adding the iron salt or its solution to a solution containing carbonic acid and/or hydrogencarbonic acid and lactoferrins.

The resultant lactoferrin complexes are highly heat resistant and useful as raw materials of foods, medicines, feeds, cosmetics and so forth.

14 Claims, No Drawings

IRON LACTOFERRIN COMPLEXES AND PREPARATION THEREOF

This application was filed under 35 U.S.C. §371 as a request for U.S. examination of International application No. PCT/JP94/00233 filed on Feb. 16, 1994 and published as WO94/19375 Sep. 1, 1994.

FIELD OF THE INVENTION

This invention relates to thermally stable and heat resistant iron lactoferrin complexes bound with a large quantity of and preparation thereof.

The heat resistant lactoferrin complexes of the present invention contain a large quantity of iron, show no iron specific astringent taste, and prevent the acceleration of peroxide formation by iron. Thus, the complexes are useful as raw materials of foods, medicines, feeds, cosmetics and so forth for the prevention and treatment of anemia, the enrichment of iron content, or the prevention of the infection by pathogenic microorganisms.

BACKGROUND OF THE INVENTION

Various physiological activities of lactoferrin (hereinafter abbreviated as Lf) such as acceleration of iron absorption, prevention of lipoperoxide formation, antibacterial and antiviral activity, cell proliferation, and control of immune system have been known. Therefore, Lf has been used in the production of foods, medicines, feeds and cosmetics. These products are generally pasteurized thermally, or treated with boiled water before use.

However, Lf has an essential drawback of instability against heat. Heat treatment causes precipitation of Lf due to thermal denaturation, and loss of iron binding property which leads to a physiologically inactive state. Investigation for the stabilization of Lf against heat was carried out and revealed that heating at pH 4 does not affect the binding property of Lf to iron (Davidson and Lonnerdal. Am. J. Physiol., 257: G930-G934, 1989). However, heat treated Lf at pH 4 gradually degenerates and loses its physiological properties. Additionally, heat treated of Lf under low ionic strength maintained its physiological activity (Japanese Laid-open Patent Application No. 108629/1992). However, practical ionic strength in commonly used products is not necessarily low. The relative effect on heat stability of Lf to pH and electric conductivity, $\Omega$, was investigated to develop a method of preparation of heat resistant of Lf and showed stabilization of Lf solutions against heat by adjusting log $\Omega$ to satisfy the following equations (Japanese Laid-open Patent Application No. 8269/1992).

$$\log \Omega \geq (2.96/\text{pH})+0.64 \quad (\text{pH}<5)$$

$$\log \Omega \geq (29.37/\text{pH})-4.62 \quad (5 \geq \text{pH} \geq 7.9)$$

$$\log \Omega \geq -0.917 \quad (\text{pH}>7.9)$$

Lf solutions out of the ranges mentioned above require separate pasteurization of Lf solutions and the other raw material solutions followed by aseptic mixing of the pasteurized solutions. Japanese Regulations demand single pasteurization by heating after mixing, and does not allow separate pasteurization and mixing.

DISCLOSURE OF THE PRESENT INVENTION

The inventors have been investigating to solve the problems mentioned above for the stabilization of Lf against heat and concluded that it is necessary to modify Lf itself to give heat resistance while maintaining iron binding property. The inventors have prepared heat resistant iron-Lf complexes by reacting of iron salt solution containing carbonic acid or hydrogencarbonic acid ion with Lfs solutions. The iron salt solution must have pH$\leq$4 when dissolved in water to give the heat resistant complexes with Lf and carbonic acid or hydrogencarbonic acid ion. Therefore, one object of the present invention is to provide heat resistant carbonate- and/or hydrogen-carbonate-iron-Lf complexes. One other object of the present invention is to provide processes for the preparation of heat resistant carbonate- and/or hydrogen-carbonate-iron-Lf complexes.

That is, the present invention relates to heat resistant iron-Lf complexes in which Lfs are bound with iron via carbonic acid and/or hydrogencarbonic acid.

Additionally, the present invention relates to processes for the preparation of heat resistant iron-Lf complexes. An aqueous solution of Lf is mixed with iron salt, which shows pH$\leq$4 when dissolved in water, or an aqueous solution in which are dissolved Lf together with the iron salt. The aqueous solution is made pH$\leq$7 by adding salt(s) containing carbonic acid ion or hydrogencarbonic acid ion that bind iron ion to Lf via carbonic acid ion and/or hydrogencarbonic acid ion.

The heat resistant iron-Lf complexes of the present invention exhibit excellent heat resistance and are soluble under pH$\leq$7.

However, the obtained complexes 1) precipitate under pH$\geq$7.1 and 2) slowly became insoluble under storage at pH$\leq$7 when 150 or more molecules of iron are bound to one molecule of Lf.

Therefore, one further object of the present invention is to provide heat resistant Lf complexes and processes for the preparation thereof which are stable for a long period of time under wide range of pHs.

The inventors have been investigating to solve the problems mentioned above and found that 1) carbonate- and/or hydrogen-carbonate-iron-Lf complexes are formed by mixing a solution containing carbonic acid and/or hydrogencarbonic acid ion with Lfs and an iron salt, and that 2) the complexes can be formed by adding Lfs and an iron salt solution to carbonic acid and/or hydrogencarbonic acid ion solution until Lf- and iron- (hydrogen)carbonic acid ratios reached a particular range. The resultant heat resistant complexes contain iron at high ratios and are stable under wide range of pHs for a long period of time. Furthermore, the inventors found that the complexes are heat resistant without iron specific astringent taste, prevent acceleration of peroxide formation of iron.

One further characteristic feature of the present invention relates to carbonate- and/or hydrogencarbonate-iron-Lf iron-Lf complexes having 15-1,000 molecules or iron and 15 molecules or over of carbonic acid and/or hydrogencarbonic acid to one molecule of Lf.

These Lf complexes form no precipitate and no characteristic astringent taste of iron, when they are stocked at pH 2.1-9.0 for at least one month at ordinary temperature and treated with high temperatures.

The present invention further relates to the processes for the preparation of these iron Lf complexes.

The is the present invention relates to processes for the preparation of carbonate- and/or hydrogencarbonate-iron-Lf complexes by mixing solution A composed of i) a carbonate, or ii) a hydrogen-carbonate, or iii) carbonate and hydrogen-carbonate and solution B composed of iv) iron and v) Lfs to give carbonate- and/or hydrogencarbonate-iron-lactoferrin complexes having the following characteristic features of 1) to 4) described below.

However, vi) the molar concentration of iron ion in solution B is ⅓ or less of viii) molar concentrations of carbonic acid and hydrogencarbonic acid ions in a mixed reaction solution of vii) solution A and whole or part of solution B. The molar concentration of ix) Lfs in solution B is $1/15–1/1,000$ to that of x) iron ion in solution B, and $1/50$ or less to molar concentrations of xi) carbonic acid and hydrogencarbonic acid ions in the mixed reaction solution.

1) the complexes contain 15–1,000 molecules of iron and 15 or more molecules of carbonic acid and/or hydrogencarbonic acid to one molecule of Lfs,
2) the complexes form no precipitate at least for one month under pH 2.1–9.0 at ordinary temperatures,
3) the complexes form no precipitate by heating, and
4) the complexes have no iron specific astringent taste.

Furthermore, the present invention relates to process for preparation of carbonate- and/or hydrogencarbonate-iron-Lf complexes by mixing a solution A containing i) carbonic acid, ii) hydrogencarbonic acid or iii) carbonic acid and hydrogencarbonic acid and iv) Lfs and a solution B containing v) iron to give carbonate- and/or hydrogencarbonate-iron-Lf complexes having the following characteristic features of 1) to 4) described below.

However, vi) the concentration of in solution B iron ion is $1/3$ or less of vii) molar concentrations of carbonic acid and hydrogencarbonic acid ions in a mixed reaction solution of viii) solution A and whole or part of solution B. The molar concentration of ix) Lf in solution A is $1/15–1/1,000$ to that of x) iron ion in solution B, and $1/50$ or less to molar concentrations of xi) carbonic acid and hydrogencarbonic acid ions in the mixed reaction solution.

1) the complexes contain 15–1,000 molecules of iron and 15 or more molecules of carbonate and/or hydrogencarbonate to one molecule of Lfs,
2) the complexes form no precipitate at least for one month under pH 2.1–9.0 at ordinary temperatures,
3) the complexes form no precipitate by heating, and
4) the complexes have no iron specific astringent taste.

The Lfs used in the present invention include Lfs isolated from milk of mammals such as human beings and cows, transferrin isolated from blood or viscera, and ovotransferrin isolated from eggs. These Lfs are massively isolated by several known methods and any Lf obtained by one of these procedures can be used. Furthermore, Lfs produced by genetic engineering methods using microorganisms, animal cells or transgenic animals may also be used.

Hydrolyzed Lfs by enzyme can be used for Lf. Complete purification of Lfs is not required and crude compounds containing some other components may also be used.

In the first invention, iron salts which show pH≦4 when dissolved in water are used, for example, $FeCl_3$, $Fe(NO_3)_3$ and $Fe_2(SO_4)_3$ are enumerated. Other iron salts that show pH>4 when dissolved in water can not provide heat resistance even after adjustment to pH≦4 by the addition of an acid. In the present invention, iron salts are used in amounts ranging 20–500 mg, preferably 40–500 mg of iron ion per one g of LF. The amount of iron over 500 mg result in partial precipitation of iron with Lf.

The alkali salts used in the present invention are salts including carbonic acid ion or hydrogencarbonic acid ion. Ammonium carbonate, sodium carbonate, potassium carbonate and the like are examples of alkali salts containing carbonic acid ion. Ammonium hydrogencarbonate, sodium hydrogencarbonate, potassium hydrogencarbonate and the like are examples of alkali salts containing hydrogencarbonic acid ion. These alkali salts may be used concurrently with conventional alkali hydroxides such as NaOH, ammoniac and KOH. An alkali salt releasing hydrogencarbonate ion may for the adjustment of pH during the preparation. be used for the adjustment of pH during the preparation However, equimolar amount of hydrogencarbonic acid ion to iron bound to Lf is essential, that is 22–562 mg, preferably 35–400 mg of hydrogencarbonic acid ion to one g of Lf. Therefore, 120 mg to five g, preferably 350 mg to five g of alkali hydrogencarbonate to one g of Lf shall be added to a mixed solution of Lf and, iron salt. Addition of hydrogencarbonate in an amount less than 350 mg, particularly less than 120 mg reduces the amount of iron that bind with Lf via hydrogencarbonic acid ion and leads to insufficient heat resistant Lf. On the other hand, amount of hydrogencarbonic acid ion over five g causes precipitation due to the excess of hydrogencarbonic acid ion and iron. Final heat resistant Lf-iron salt solution shall be pH≦7, or else precipitates will be formed.

The iron-Lf complexes of the present invention with heat resistance have different surface structure from that of natural Lf. Lf contains a number of basic amino acids such as lysine and arginine and positive charges by acidification with the addition of an iron compound. The positively charged Lf binds with hydrogencarbonic acid ion and iron successively and forms heat resistant iron-Lf complex of the present invention. The heat resistant iron-Lf complexes are stable even by heating at 90° C.

Generally, formation of an iron saturated type Lf by mixing with an iron salt and a hydrogencarbonate has been known for a long time. This iron saturated type Lf has a structure of two similar regions of N lobe and C lobe which bind with one molecule of iron, respectively. The N lobe has four amino acid residue of Asp60, Tyr92, Tyr192 and His253 (in which numerals indicate the order of amino acid from N-terminal) bound with one molecule of iron ion and one hydrogencarbonic acid. Similarly, the C lobe has Asp395, Tyr435, Tyr528 and His597 which bind with iron ion (B. F. Anderson et al., J. Mol. Biol., 209, 711–734, 1989). Therefore, iron saturated type Lf generally binds with 1.4 mg of iron and 1.5 mg of hydrogencarbonic acid ion, respectively, for one g of Lf and has a slight increase of stability in comparison to iron free Lf, but precipitates by heating at 65° C. or higher.

Furthermore, addition of a large amount of iron to Lf forms iron-Lf binding losing free iron and provides a stabilized iron solution (Japanese Laid-open Patent Application No. 141067/1992). However, no heat resistance of Lf by the addition of a large amount of iron or use of a carbonate or a hydrogencarbonate is disclosed. No example of the above mentioned Japanese Laid-open Patent Application discloses the use of a carbonate or a hydrogencarbonate. Therefore, heat resistant iron-Lf complexes of the present invention having Lf bound with iron via a carbonic acid ion and/or a hydrogencarbonic acid ion are quite different from those of known compounds.

The heat resistant iron-Lf complexes of the present invention contain far more iron and hydrogencarbonic acid ion than those of so-called iron saturated type Lf forming an armor-like cladding. Thus, the heat resistant iron-Lf complexes of the present invention are difficultly recognized by an antibody because of the iron armor.

The antibody recognition test of the heat resistant iron-Lf complexes of the present invention is shown below:

Test experiment 1

In a citrate buffer, bovine Lf was dissolved. Iron was removed from the solution, which was dialyzed against water to give two mg/ml of bovine Lf solution. The solution was mixed with various amounts of $FeCl_3$ and added with 0.12–0.5 g of $NaHCO_3$ for one g of Lf to adjust to pH 6.5. The resulting bovine Lf solution was mixed with equal amounts of 0.1M imidazole buffer having pH 6.6 containing 0.3M NaCl. Separately, a plate for ELISA was coated with anti-bovine Lf antibody, blocked with BlockAce (Dainippon Pharmaceutical Co., Ltd.) and added with the bovine Lf solution prepared above. The mixture was caused to react for one hr. at room temperature, then anti-bovine Lf antibody labeled with peroxidase was caused to react. After the reaction, the plate was washed thoroughly, and ADTS substrate was added. An absorbance rate at 405 nm was determined. The antibody recognition rate at various concentrations of an iron salt are shown in Table 1.

TABLE 1

| Iron salt added (mg/g Lf) | Recognized Lf with the antibody (mg/ml) |
|---|---|
| 0 | 1.02 |
| 1.4 | 1.02 |
| 20 | 0.95 |
| 40 | 0.82 |
| 50 | 0.57 |
| 60 | 0.50 |
| 70 | 0.36 |
| 80 | 0.20 |
| 100 | 0.09 |

As shown above, the concentration of Lf at which Lf is recognized by the antibody decreased with the increase of iron salt bound to Lf via hydrogencarbonic acid ion. Preparation o f an Lf and iron solution was tried using NaOH instead of $NaHCO_3$ and adjusting pH 6.5 as a control solution, but precipitates were formed and could not be used for ELISA.

Heat stability of Lf was tested using various iron salts.

Test experiment 2

Various iron salts shown in the Table 2 mentioned below was added to Lf solution to prepared iron ion ratio of 120 mg to one g of Lf and adjusted to pH 6.3 with 1M $NaHCO_3$ solution. The obtained solution was mixed with imidazole to give final concentration of 0.05M imidazole and 0.15M NaCl, pH 6.6, heated at 90° C. for 10 min., and precipitation of Lf was mentioned. The results are shown in Table 2.

TABLE 2

| Iron salt | pH at iron concentration of 120 μg/ml in water | Precipitation |
|---|---|---|
| $Fe(NO_3)_3$ | 2.73 | No, clear |
| $FeSO_4$ | 4.81 | Yes |
| $FeCl_3$ | 2.69 | No, clear |
| $FeCl_2$ | 4.56 | Yes |
| $FeCl_2$ | 4.56 → 2.66 (adjusted with HCl) | Yes |
| $Fe(SO_4)NH_4$ | 4.83 | Yes |
| $Fe_2(SO_4)_3$ | 2.60 | Yes, slightly turbid |
| Iron pyrophosphate | 6.80 | Yes |
| Iron citrate | 6.53 | Yes |
| Iron fumarate | 4.50 | Yes |
| Iron fumarate | 4.50 → 2.75 (adjusted with HCl) | Yes |

As shown above, (1) iron salts exhibiting pH≦4 when dissolved in water provided heat resistance to Lf, but the other iron salts could not provide heat resistance to Lf, (2) iron salt exhibiting pH>4 when dissolved in water could not provide heat resistance regardless of adjustment to pH≦4 with an acid, and (3) iron salts must be added within a predetermined amount.

Lf complexes of the present invention at approximately neutral pH region exhibit heat-resistance differently from those in Japanese Laid-open Patent Application No. 141067/1992.

Test experiment 3

In 15 ml of an Lf aqueous solution at concentration of 2.7 mg/ml, $FeCl_3$ was added so as to have final iron ion concentrations of 20–1,000 μg/ml, 4–210 mg of $NaHCO_3$ was added to adjust to pH 6.2 and give iron-Lf complexes. of the present invention. Separately, to 15 ml of $FeSO_4 \cdot 7H_2O$ aqueous solution at concentrations of 20–1,000 μg/ml was added Lf to give a concentration of 2.7 mg/ml according to Japanese Laid-open Patent Application No. 141067/1992. During the procedure, hydrogencarbonate solution was not used. The resultant solutions were diluted to 20 ml with water and an aliquot of eight ml of the solution was mixed with eight ml of buffer solution (0.1M imidazole, HCl and 0.3M NACl, pH 6.6 or pH 7.3). The mixed solutions were adjusted to pH 6.5 or 7.2. The solutions so obtained were 90° C. for 10 min., allowed to cool to room temperature, centrifuged at 3,000 rpm for 10 min. and the Lf content in the supernatant was determined with Protein Assay (Bio-Rad Co., Ltd.). The ratios of Lf remaining in the supernatants are shown in Table 3.

TABLE 3

| Iron salt added | Japanese Laid-open Patent Application No. 141067/1992 | | The present invention | |
|---|---|---|---|---|
| (Iron mg/g Lf) | pH 6.5 | pH 7.3 | pH 6.5 | pH 7.3 |
| 10 | 5% | 3% | 40% | 40% |
| 20 | 6 | 4 | 73 | 46 |
| 30 | 6 | 4 | 81 | 40 |
| 40 | 5 | 4 | 96 | 38 |
| 50 | 7 | 3 | 100 | 34 |
| 100 | 5 | 4 | 100 | 50 |
| 500 | 3 | 4 | 94 | 21 |
| 1,000 | 3 | 3 | 28 | 11 |

As shown above, the heat resistant iron-Lf complexes of the present invention exhibited heat stability of 73% or higher in the range of 20–500 mg and 90% or higher in the range of 40–500 mg of total iron content for one g of Lf at pH≦7 in the final solution.

The heat resistant iron-Lf complexes of the present invention have no particular restrictive conditions for the preparation of products containing the complexes. However, the complexes are preferably used for the products having following relationships between final pH and electric conductivity Ω:

$$\log \Omega > (2.96pH) + 0.64 \quad (4 \leqq pH < 5)$$

$$\log \Omega > (29.37/pH) - 4.62 \quad (5 \leqq pH \leqq 7).$$

When the pH and electric conductivity Ω are out of the range of the relationships mentioned above, then a known pasteurization method (Japanese Laid-open Patent Application No. 8269/1992) can be satisfactorily used, and when the pH resides at pH>7, the heat resistant Lf of the present invention can not be obtained. Some amount of an acid may be added to make adjust pH≦7 when the products show pH>7. Then the products can be thermally pasteurized or sterilized by conventional methods. Thermal treatment is performed by low temperature heating at 65° C. for 30 min., or 120° C. for 2–3 sec. or 140°–150° C. for 3–5 sec., or by retort treatment. Evaporation may provides powder preparations containing heat resistant Lf-iron complexes. Lyophilization may also be used to give dried products, but low cost spray drying is preferable for the preparation of a large amount of products.

The heat resistant iron-Lf complexes obtained by these procedures contain iron and are preferably used for the prevention and treatment of anemia as food and feed additives and medicines. The complexes are suitable to prepare pathogen free medicines (Japanese Laid-open Patent Application No. 220130/1991), feeds, foods and cosmetics. The heat resistant iron-Lf complexes of the present invention are preferably used for the preparation of iron enriched drinks as they give out scarcely any odor of iron despite of their iron content.

In the second invention of the present patent, aqueous solutions containing a carbonate and/or a hydrogencarbonate for the preparation of lactoferrin complexes can be illustrated by carbonated water, $NH_4HCO_3$, $NaHCO_3$, $KHCO_3$, $Na_2CO_3$, $CaCO_3$ or their mixed solutions. Furthermore, NaOH, ammoniac, KOH, HCl, citric acid, lactic acid and so forth may be added as a pH adjusting agent. The solutions may optionally contain other compounds such as sugars, proteins and fats.

The iron compounds which exhibit $pH \leq 4$ when dissolved deionized water can be used to prepare the complexes and mainly include trivalent iron compounds, for example, $FeCl_3$, $Fe(NO_3)_3$ and $Fe_2(SO_4)_3$. Iron salts which exhibit $pH > 4$ when dissolved in deionized water, for example $FeSO_4$, can not form the Lf complexes even if the solution was made $pH \leq 4$.

An iron compound is added to one mole of Lf at ratios of 15 moles or more, preferably 30 moles or over, more preferably 60–1,000 moles, and suitably at 480 moles or less. Furthermore, 240 moles or less is preferable to shorten the reaction period without decline in yield. An excess amount of iron compound will form precipitates containing iron.

The differences the stability of lactoferrin complexes of the second invention caused by the kind of iron salts used were evaluated by the following test experiment.

Test experiment 4

(Materials)

(Solution A) One L of 1 mole/L $NaHCO_3$ solution, pH 8.3.
(Solution B1) 0.2 L of various iron salt solutions containing five milli-moles of iron.
(Solution B2) 0.8 L of solution containing 33 μmoles of Lf (Oreofina Co., Ltd.)

Solutions B1 and B2 were mixed to give solution B. The solution B added to solution A to was give an iron-Lf complex. The resultant solution was desalted and condensed with an ultrafiltration membrane with 5,000 moleculars weight cut. The condensed solution was diluted with a sham buffer containing 0.05M imidazole buffer containing 0.15M NaCl at pH 7.5 to give 3.6 mmole/L of iron concentration and heated at 90° C. for 10 min. The formation of precipitates was monitored. The results are shown in Table 4.

TABLE 4

| Iron salt | pH at iron concentration of 120 μg/ml in deionized water | Precipitation |
|---|---|---|
| $Fe(NO_3)_3$ | 2.7 | No |
| $FeSO_4$ | 4.8 | Yes |
| $FeCl_3$ | 2.7 | No |
| $FeCl_2$ | 4.6 | Yes |
| $Fe(SO_4)NH_4$ | 4.8 | Yes |
| $Fe_2(SO_4)_3$ | 2.6 | No |
| Iron pyrophosphate | 6.8 | Yes |
| Iron citrate | 6.5 | Yes |
| Iron fumarate | 4.5 | Yes |
| $FeSO_4$ | 4.8 → 2.7 (adjusted with HCl) | Yes |

As shown above, no carbonate- and/or hydrogencarbonate-iron-Lf complex could be obtained without using iron salt showing $pH \leq 4$ in a deionized aqueous solution. Furthermore, carbonate- and/or hydrogencarbonate-iron-Lf complex could not be obtained even by adjustment to $pH \leq 4$ when an iron salt which show $pH > 4$ in a deionized aqueous solution was initially used.

The ratio of iron ion to carbonic acid and/or hydrogencarbonic acid ion greatly influences on the heat stability of carbonate- and/or hydrogencarbonate-iron-Lf complexes. The following test experiment will show the role of the ratio.

Test experiment 5

(Materials)

(Solution A) One L of $NaHCO_3$ at various concentrations.
(Solution B1) 0.2 L of $FeCl_3$ solutions.
(Solution B2) 0.8 L of solution containing one milli-mole of Lf.

Solutions B1 and B2 were mixed to give solution B. The solution B was diluted with deionized water and then added to solution A to give Lf bound with iron. However, when the final hydrogencarbonic acid ion was made 0.6M or over, $NaHCO_3$ was added during the mixing procedure of solutions A and B, or a required amount of $NaHCO_3$ was previously added to the solution A, which was saturated before addition of solution B. The obtained solution was desalted and condensed with an ultrafiltration membrane with molecular weight cut of 5,000, and diluted with the sham buffer to give 3.6 mmole/L of iron concentration. The diluted solutions were heated at 90° C. for 10 min. and the formation of precipitates of Lf was monitored. The results are shown in Table 5. The minimum ratio of hydrogencarbonic acid ion to iron in the Table 5 was calculated by dividing the molar concentration of hydrogencarbonic acid of the mixture of solutions A and B with iron concentration in solution B.

TABLE 5

Solution B1 containing 30 milli-mole of iron

| Molar concentration of hydrogencarbonic acid ion | | | Minimum ratio of hydrogencarbonic acid ion to iron (mole/mole) |
|---|---|---|---|
| Solution A | Mixed solution of A and B | Precipitates | |
| 1.0 | 0.5 | No | 16.67 |
| 0.8 | 0.4 | No | 13.33 |
| 0.6 | 0.3 | No | 10.00 |
| 0.4 | 0.2 | Slight | 6.67 |
| 0.2 | 0.1 | Slight | 3.33 |
| 0.1 | 0.05 | Yes | 1.67 |

TABLE 6

Solution B1 containing 200 milli-mole of iron and 10-fold diluted solution B (Solution B contained 20 mmole/L of iron)

| Molar concentration of hydrogencarbonic acid ion | | | Minimum ratio of hydrogencarbonic acid ion to iron (mole/mole) |
|---|---|---|---|
| Solution A | Mixed solution of A and B | Precipitates | |
| Saturated | Saturated | No | over 120 |
| Saturated | 1.2 | No | 120 |
| Saturated | 1.0 | No | 100 |
| Saturated | 0.8 | Faint | 80 |
| Saturated | 0.7 | Faint | 70 |
| 1.2 | 0.6 | Faint | 60 |
| 1.0 | 0.5 | Slight | 50 |
| 0.6 | 0.3 | Slight | 30 |
| 0.3 | 0.15 | Yes | 15 |

As shown above, a higher concentration of hydrogencarbonic acid ion in the mixed solutions A and B was required with the use of a higher iron concentration in solution B. Thus, for the preparation of the carbonate- and/or hydrogencarbonate-iron-Lf complexes, at least three molecules, preferably 10 molecules or over of carbonate and/or hydrogencarbonate are required around one molecule of iron during the addition of the solution B to the solution A. Furthermore, 30 molecules or over, preferably 60 molecules or over, more preferably 100 molecules or over of carbonic acid and/or hydrogencarbonic acid ions around one molecule of iron are necessary to bind one molecule of Lf with more than 200 molecules of iron.

The following test experiment was carried out to investigate how much carbonate and/or hydrogencarbonate is necessary to prepare the carbonate- and/or hydrogencarbonate-iron-Lf complexes of the present invention.

Test experiment 6

(Materials)

(Solution A) One L of $NaHCO_3$ at various concentrations.
(Solution B1) 0.2 L of solution containing 100 mmole $FeCl_3$.
(Solution B2) 0.8 L of solution containing one mmole Lf.

Solutions B1 and B2 were mixed to give solution B. The solution B was added to solution A at 4° C. and 37° C. with gentle stirring to give Lf bound with iron. The resultant solution was diluted with the sham buffer to give 3.6 mmole/L iron solution and heated at 90° C. for 10 min. to observe the formation of precipitates of Lf. In addition, the reaction mixture reacted for 192 hrs., then was filtered with an ultrafiltration membrane of 5,000 molecular weight cut to separate carbonate- and/or hydrogencarbonate-iron-Lf complexes from the aqueous solution. The concentration of carbonic acid and hydrogencarbonic acid ions in the filtrate was determined by ion chromatography. The results are shown in Table 7-1 and Table 7-2

As shown above, the complexes of carbonate- and/or hydrogencarbonate-iron-Lf the present invention can be formed under low temperatures for a long period of reaction at an equal ratio of carbonate and hydrogencarbonate ion to iron. However, lower concentrations of carbonate and hydrogencarbonate ion do not give the desired complexes even after a long period of reaction. Furthermore, when one or less was the minimum ratio of hydrogencarbonic acid ion to iron in the filtrate of ultrafiltration after reaction for 192 hrs., the concentrations of carbonic acid and hydrogencarbonic acid ions in the filtrate became equal with those in the deionized water, providing complete formation of all hydrogencarbonate in solution A with iron-Lf complexes. No complex can be formed under the reaction condition of carbonic acid and hydrogencarbonic acid ions/iron ratios of two or less at 37° C.

Above results indicate that the carbonate- and/or hydrogencarbonate-iron-Lf complexes of the present invention contain one or more molecules of carbonic acid and/or hydrogencarbonic acid ions to the bound molecule of iron. Increased concentrations of carbonic acid and/or hydrogencarbonic acid ions clearly accelerated the reaction rate of the formation of carbonate- and/or hydrogencarbonate-iron-Lf complexes.

TABLE 7-1

Reaction temperature at 4° C.

| Molar concentration of hydrogencarbonic acid ion | | Minimum ion ratio of hydrogencarbonic acid ion to iron (mole/mole) | Precipitation Reaction period (hrs.) | | | | | Concentration of hydrogencarbonic acid ion in filtrate (mmole/L) |
|---|---|---|---|---|---|---|---|---|
| Solution A | Mixed solution of A and B | | 2 | 24 | 48 | 96 | 192 | |
| 1.2 | 0.6 | 6 | No | No | No | No | No | 0.4654 |
| 0.8 | 0.4 | 4 | No | No | No | No | No | 0.2630 |
| 0.4 | 0.2 | 2 | Yes | No | No | No | No | 0.0988 |
| 0.2 | 0.1 | 1 | Yes | Yes | Yes | No | No | 0.0005 |
| 0.1 | 0.05 | 0.5 | Yes | Yes | Yes | Yes | Yes | 0.0007 |
| 0.05 | 0.025 | 0.25 | Yes | Yes | Yes | Yes | Yes | 0.0004 |

TABLE 7-2

Reaction temperature at 37° C.

| Molar concentration of hydrogencarbonic acid ion | | Minimum ratio of hydrogencarbonic acid ion to iron (mole/mole) | Precipitation Reaction period (hrs.) | | | | |
|---|---|---|---|---|---|---|---|
| Solution A | Mixed solution of A and B | | 2 | 24 | 48 | 96 | 192 |
| 1.2 | 0.6 | 6 | No | No | No | No | No |
| 0.8 | 0.4 | 4 | No | No | No | No | No |
| 0.4 | 0.2 | 2 | Yes | Yes | Yes | Yes | Yes |
| 0.2 | 0.1 | 1 | Yes | Yes | Yes | Yes | Yes |
| 0.1 | 0.05 | 0.5 | Yes | Yes | Yes | Yes | Yes |
| 0.05 | 0.025 | 0.25 | Yes | Yes | Yes | Yes | Yes |

Above experiments also showed that iron-Lf complexes can be formed when i) the iron ion molar concentration in solution B was equal to iii) molar concentration of carbonic acid and/or hydrogencarbonic acid ions in ii) a mixture of solution A and part or whole of solution B (reaction solution). But this condition requires extremely long reaction period and is naturally impractical.

Kawakami et al. solubilized iron by mixing i) 900 μl of 86 mmole/L $FeCl_3$ and 1.23–55.56 mmole/L Lf and ii) 100 μl of 0.2 mole/L of $NaHCO_3$ (H. Kawakami, S. Dosako and I. Nakajima, Biosci. Biotech. Biochem., 57: 1376–1377, 1993). In the report, their heat resistance and taste were not examined and their iron ion concentration differed from that of the present invention. Therefore, the disclosure in the report is out of the scope of the present invention but the present invention is compared with the disclosure for reference.

Particular mixing method of two solutions is not disclosed in the report, but generally two solutions would have been mixed at once or nearly at once. The mixed solution (reaction solution) contains 0.02 mole/L of carbonic acid and hydrogencarbonic acid ions and the concentration of iron in the solution of $FeCl_3$ is 86 mmole/L. The minimum ratio of hydrogencarbonic acid ion to iron is 0.23. This ratio approximately corresponds to the minimum ratio of hydrogencarbonic acid ion and iron of 0.25 with reaction period of 48 hrs. in Table 7-2, which condition can not provides heat resistance to Lf. Using solutions whose compositions are the same as those disclosed in Kawakami et al. The heat-resistant Lf-complexes of this invention might be obtained if the following procedure are performed. Firstly mix 133 μl of solution i) with solution ii) at 4° C. for 96 hrs. Then, add remaining 767 μl of solution i) to the mixture. In the first step of this procedure, the concentration of carbonic acid and hydrogencarbonic acid ions is equivalent to 86 mmole/L of $FeCl_3$ in solution i). The minimum ratio of hydrogencarbonic acid ion to iron is one, which corresponds to the fourth row at reaction time 96 hrs. in Table 7-1. Therefore, the first step may provides heat resistant iron-Lf complex at a particular rate of 14.8% (133 μl/900 μl ). However, the remaining Lf in the second step will not acquire heat resistance. No such reaction procedure is disclosed in Kawakami et al. In addition, the reaction temperature is 37° C., therefore, no heat resistant iron-Lf complex is expected in view of the present test experiment.

One further important factor which affect the heat stability of the complexes is a concentration ratio of Lf and carbonic acid and/or hydrogencarbonic acid ions. The factor was investigated in the following test experiment.

Test experiment 7

(Materials)

(Solution A) One L of $NaHCO_3$ solutions at various concentrations.

(Solution B1) 0.2 L of solution containing 1.5 mmole $FeCl_3$.

(Solution B2) 0.8 L of solution containing 0.5 mmole Lf.

Solutions B1 and B2 were mixed to give solution B. The solution B was added to solution A to prepare iron bound Lf complex. The resulting solution was desalted and then condensed with an ultrafiltration membrane of 5,000 molecular weight cut. Furthermore, the condensed solution was diluted with the sham buffer to make 3.6 mmole/L of iron concentration. The diluted solution was heated at 90° C. for 10 min. The formation of precipitates of Lf was monitored. The results are shown in Table 8. The minimum ratio of hydrogencarbonic acid ion to Lf was calculated by dividing molar concentration of hydrogencarbonic acid ion in a mixture of solutions A and B, with molar concentration of Lf in solution B.

TABLE 8

| Concentration of hydrogen-carbonic acid ion (mmole/L) | | | Minimum ratio of hydrogen-carbonic acid ion to Lf (mole/mole) | Minimum ratio of hydrogen-carbonic acid ion to iron (mole/mole) |
|---|---|---|---|---|
| Solution A | Mixed solution of A and B | Precipitates | | |
| 200 | 100 | No | 200 | 67 |
| 100 | 50 | Faint | 100 | 33 |
| 50 | 25 | Slight | 50 | 17 |
| 30 | 15 | Yes | 30 | 10 |
| 10 | 5 | Yes | 10 | 3.3 |

As shown above, requirement for the presence of at least molecules, preferably 100 molecules, more preferably 200 molecules of carbonic acid and/or hydrogencarbonic acid (ions) around one molecule of Lf in the solution is clearly indicated.

The Lf complexes of the present invention contain far more bound iron, and carbonate and/or hydrogencarbonate in comparison to so-called conventional iron saturated type Lf which has two molecules of iron bound to Lf in Anderson et al.

Addition of a large amount of iron to provide heat resistance to Lf, or requirement of carbonic acid ion or hydrogencarbonic acid ion or use of carbon dioxide, carbonate or hydrogencarbonate is not disclosed in Japanese Laid-open Patent Application No. 141067/1992. Therefore, the carbonate- and/or hydrogen-carbonate-iron-Lf complexes of the present invention is quite different from the known art shown above.

The carbonate- and/or hydrogencarbonate-iron-Lf complexes of the present invention are considered to have modified high order Lf structures such as tertiary or quaternary structure with carbonate and/or hydrogencarbonate and iron, or structures in which Lf is surrounded with carbonate and/or hydrogencarbonate and iron. In fact, the recognition rate of the carbonate- and/or hydrogencarbonate-iron-Lf complex of the present invention by anti-Lf antibody which generally recognizes iron saturated Lf declines with the increase of binding of carbonate and/or hydrogencarbonate and iron with Lf. The decline is shown by the following test experiment.

Test experiment 8

Lf sample was obtained by dialysis of Lf solution against citrate buffer containing 0.1% ethylenediamine tetraacetic acid (EDTA) to remove iron, and dialysis against water, followed by lyophilization. Solution A: one L of one mole/L $NaHCO_3$, pH 8.3, solution B1: 0.2 L of solution containing 0–480 mmole $FeCl_3$ and solution B2: 0.8 L of solution containing one mmole of Lf were prepared. Solutions B1 and B2 were mixed and this mixture was diluted with one to 100-fold with deionized water to give solution B. One L of solution B was added to one L of solution A to give iron bound Lf solution. The resulting solution was serially diluted 2-fold with the sham buffer Separately, an ELISA plate was coated with anti-bovine Lf antibody, blocked with BlockAce (Dainippon Pharmaceutical Co., Ltd.). Then the Lf solution prepared above was added to the plate and incubated for one hr. at room temperature, followed by reacting with anti-bovine Lf antibody labeled with peroxidase successively. The plate was thoroughly washed, ABTS substrate was added and the absorption rate at 405 nm was determined. When two molecules of iron was bound with Lf, Lf was recognized similarly to those without containing iron, but Lf became not recognizable with the increase of iron content. The results are shown in Table 9. The recognition rate in the Table is the ratio of quantity determined by this ELISA to the amount of Lf contained in iron-Lf solution.

TABLE 9

| Iron (mole/mole Lf) | Recognition rate (%) |
|---|---|
| 0 | 100 |
| 2 | 100 |
| 15 | 90 |
| 30 | 86 |
| 60 | 82 |
| 90 | 60 |
| 120 | 31 |
| 150 | 19 |
| 240 | 14 |
| 480 | 14 |

Above mentioned Lf complexes (hereinafter abbreviated as Lf complex of the second invention) are different from the previously mentioned Lf complex (hereinafter abbreviated as Lf complex of the first invention) in stability with pH, and further different from that of Lf disclosed in Japanese Laid-open Patent Application No. 141067/1992. The differences will be shown by the following experiment.

Test experiment 9

The Lf complex of the second invention was prepared in a similar manner with that of test experiment 8. The Lf complex of the first invention was prepared by adding $FeCl_3$ to 33.75 mmole/L of Lf aqueous solution to give iron content of 0.5–16.2 mmole/L and adjusted to pH 6.2 with $NaHCO_3$. Furthermore, Lf solution disclosed in Japanese Laid-open Patent Application No. 141067/1992 was prepared by dissolving Lf to aqueous solution of $FeSO_4 \cdot 7H_2O$ containing 187–6,000 mmole iron/dl to give concentration of 12.5 mmol/dl. In this case, no carbonic acid and/or hydrogencarbonic acid ion, carbonate, or hydrogencarbonate was used. Various iron and Lf mixed solutions prepared by above three methods were desalted and condensed using an ultra-filtration membrane of 5,000 molecular weight cut, and diluted to give 12.5 mmole/L of Lf solutions with the sham buffer having pH 6.4 or 7.2. The resulting solutions were adjusted pH 6.5 and 7.3, respectively, poured in test tubes with screw weight cut of 5,000 and diluted with the sham buffer to adjust Lf content 62.5 mmole/L. The sham buffers were prepared from glycine-HCl for pH 2.0–3.5, acetic acid for pH 3.5–6.0, imidazole-HCl for pH 6.0–7.8 and boric acid-KCl-NaOH for pH 7.8–9.3. Conductivity was adjusted with NaCl. The diluted solutions were poured in test tubes with screw cap and sealed. The sealed solutions were heated at 90° C. for 10 min., allowed to cool to room temperature, centrifuged at 3,000 rpm for 10 min. and the Lf content in the supernatant was determined using Protein Assay Kit (Bio-Rad Co., Ltd.). The concentration of Lf remaining in the supernatant are shown in Tables 11 and 12.

TABLE 11

| Fe/Lf molar ratio | For electric conductivity at 5 milli-siemens/cm | | | | | | | | | | |
|---|---|---|---|---|---|---|---|---|---|---|---|
| | pH | | | | | | | | | | |
| | 2.0 | 2.1 | 2.5 | 3.0 | 4.0 | 5.0 | 6.0 | 7.0 | 8.8 | 9.0 | 9.2 |
| 10 | 59 | 58 | 57 | 52 | 50 | 46 | 33 | 38 | 31 | 32 | 34% |
| 15 | 50 | 73 | 74 | 72 | 71 | 75 | 76 | 80 | 77 | 72 | 45 |
| 30 | 46 | 82 | 91 | 95 | 96 | 97 | 99 | 100 | 100 | 100 | 36 |
| 60 | 51 | 95 | 93 | 97 | 98 | 100 | 100 | 100 | 100 | 100 | 43 |
| 120 | 54 | 97 | 100 | 100 | 100 | 100 | 100 | 100 | 100 | 100 | 39 |
| 240 | 32 | 99 | 100 | 100 | 100 | 100 | 100 | 99 | 99 | 97 | 40 |
| 480 | 21 | 92 | 93 | 96 | 100 | 100 | 100 | 98 | 96 | 93 | 47 |
| 1000 | 20 | 76 | 77 | 78 | 79 | 78 | 95 | 94 | 92 | 92 | 39 |
| 1200 | 19 | 32 | 28 | 31 | 33 | 27 | 29 | 30 | 24 | 33 | 32 | cap and sealed. The sealed solutions were heated at 90° C. for 10 min., allowed to cool to room temperature, centrifuged at 3,000 rpm for 10 min. and the Lf content in the supernatant was determined using Protein Assay Kit (Bio-Rad Co., Ltd.). The concentration of Lf remaining in the supernatant are shown in Table 10.

TABLE 10

| Fe/Lf molar ratio | Lf complex | | | | | |
|---|---|---|---|---|---|---|
| | Prior art[1] | | First invention | | Second invention | |
| | pH 6.5 | pH 7.3 | pH 6.5 | pH 7.3 | pH 6.5 | pH 7.3 |
| 15 | 5% | 6% | 90% | 43% | 100% | 100% |
| 30 | 7 | 6 | 84 | 40 | 100 | 100 |
| 60 | 4 | 3 | 97 | 54 | 100 | 100 |
| 120 | 6 | 1 | 98 | 38 | 100 | 100 |
| 150 | 5 | 4 | 81 | 27 | 100 | 100 |
| 240 | 9 | 2 | 79 | 21 | 100 | 100 |
| 480 | 2 | 6 | 80 | 13 | 98 | 89 |

[1]Japanese Laid-open Patent Application No. 141067/1992

As shown above, the Lf complex of the second invention exhibited heat resistance both at pH 6.5 and 7.3. However, the Lf complex of the first invention exhibited heat resistance only at pH 6.5 and no such property was found at pH 7.3. The Lf complex of the prior art showed no heat resistance at pH 6.5 or 7.3.

The pH range of heat resistance of Lf complex of the second invention will be shown in the following test experiment.

Test experiment 10

Lf complexes were prepared in similar manners with those of Test experiment 8, however, the iron content in solution B1 was extended up to 1,200 mmole.

The iron and Lf mixed solutions were desalted and condensed with an ultrafiltration membrane with molecular

TABLE 12

| Fe/Lf ratio | For electric conductivity at 150 milli-siemens/cm | | | | | | | | | | |
|---|---|---|---|---|---|---|---|---|---|---|---|
| | pH | | | | | | | | | | |
| | 2.0 | 2.1 | 2.5 | 3.0 | 4.0 | 5.0 | 6.0 | 7.0 | 8.8 | 9.0 | 9.2 |
| 10 | 51 | 50 | 52 | 53 | 49 | 46 | 37 | 34 | 31 | 32 | 31% |
| 15 | 44 | 70 | 71 | 72 | 70 | 73 | 72 | 73 | 72 | 64 | 40 |
| 30 | 41 | 73 | 82 | 85 | 85 | 85 | 87 | 88 | 89 | 87 | 34 |
| 60 | 45 | 84 | 82 | 84 | 85 | 87 | 89 | 88 | 90 | 89 | 36 |
| 120 | 47 | 87 | 89 | 90 | 90 | 90 | 90 | 92 | 91 | 88 | 34 |
| 240 | 28 | 88 | 89 | 90 | 90 | 90 | 90 | 89 | 90 | 87 | 35 |
| 480 | 20 | 79 | 82 | 83 | 81 | 83 | 86 | 85 | 82 | 80 | 41 |
| 1000 | 18 | 66 | 68 | 68 | 70 | 69 | 84 | 83 | 80 | 79 | 34 |
| 1200 | 19 | 26 | 26 | 28 | 30 | 27 | 26 | 27 | 25 | 29 | 26 |

As shown above, heat resistance was obtained only in the range of 15–1,000 molecules of iron for one molecule of Lf and was confirmed in the pH range of 2.1–9.0. Furthermore, the heat resistance was higher at 30 molecules of iron for one molecule of Lf than at 15 molecules, higher at 60 iron than at 30 molecules, even higher at 120 molecules of iron than at 60 molecules. Besides, higher heat resistance was obtained at 480 molecules of iron for one molecule of Lf than at 1,000 molecules of iron, more preferably at 240 molecules of iron than at 480 molecules of iron. For more than 1,000 molecules of iron to one molecule of Lf, pH over five gave higher heat resistance than at pH$\leq$5.

Lf produced by the first invention could not bind with 720 or more molecules of iron and caused precipitation, but the Lf complex obtained by the second invention can bind with 1,000 molecules of iron, thus the products of the second invention are different from those produced by the first invention.

Pasteurization of beverages by the prior art disclosed in Japanese Laid-open Patent Application No. 8269/1992 (herein after abbreviated as Ref. Pat.) was reported to cause precipitation or degeneration so as not to bind Lf with iron except for the ranges mentioned below of final pH and electric conductivity, $\Omega$.

$\log \Omega$ (milli-siemens/$cm$)>(2.96 $pH$)+0.64 ($pH$<5)

$\log \Omega$>(29.37 $pH$)−4.62 (5≦$pH$≦7.9)

$\log \Omega$>−0.917 ($pH$>7.9)

The Lf complexes of the present invention are very stable and heat resistant at 150 milli-siemens/cm and in the range of pH 2.1–9.0, and can be used for production of products containing them outside of the relations mentioned above of $\Omega$ and pH without causing problem. Furthermore, Ref. Pat. only discloses the pasteurization method of Lf and did not intend the formation of iron and Lf complex. Simply dissolving Lf, $NaHCO_3$ and $FeCl_3$ is shown in the example. However the present invention discloses methods of mixing, solution B composed of iv) iron and v) lactoferrins added to solution A composed of i) carbonate or ii) hydrogencarbonate, or iii) carbonate and hydrogencarbonate, or solution B composed of v) iron added to solution A composed of i) carbonate or ii) hydrogencarbonate, or iii) carbonate and hydrogencarbonate, and iv) lactoferrins. In addition, the present invention discloses the range of iron concentration in solution B. Firm iron and Lf complexes can be formed by satisfying the conditions mentioned above and providing long term stability at wide pH ranges and good heat resistance without iron specific astringent taste. Therefore, the example in Ref. Pat. could not provide a lactoferrin-iron complex, and even if the complex could be obtained, it is presumably different from that of the present invention. In fact, Ref. Pat. teaches that a beverage prepared according to the process shows bitter taste when the beverage contains 12 mg/100 ml or over of iron. On the other hand, a similar product prepared by the method of the present invention shows no bitter taste even at a concentration of 29 mg/100 ml of iron as shown later. Even if iron-Lf complexes were obtained by Ref. Pat., maximum concentration of iron in the complex is five molecules of iron to one molecule of Lf, thus, the iron-Lf complex prepared by Ref. Pat. is not within the scope of the present invention.

The Lf complex of the first invention contains 720 molecules of iron to one molecule of Lf and different from that of the second invention.

The difference in stability of the first and second inventions of the present invention will be shown in the following test experiment.

Test experiment 11

Iron-Lf complexes were prepared by similar manners with those of test experiments 9 and 10, and centrifuged Lf containing solutions were enclosed and sealed in test tubes with screw cap and heated at 90° C. for 10 min. and kept at 37° C. one month. The formed precipitates were monitored by naked eyes. No precipitate, slight precipitates and abundant precipitates were judged 0, 1 and 2, respectively.

The test results for the iron-Lf complexes prepared according to the Test experiments 9 and 10 are shown in Tables 13 and 14, respectively.

TABLE 13

| Fe/Lf molar ratio | Lf complex | | | | | |
|---|---|---|---|---|---|---|
| | Prior art[1] | | First invention | | Second invention | |
| | pH 6.5 | pH 7.3 | pH 6.5 | pH 7.3 | pH 6.5 | pH 7.3 |
| 30 | 2 | 2 | 0 | 1 | 0 | 0 |
| 60 | 2 | 2 | 0 | 2 | 0 | 0 |
| 120 | 2 | 2 | 0 | 2 | 0 | 0 |
| 150 | 2 | 2 | 2 | 2 | 0 | 0 |
| 240 | 2 | 2 | 2 | 2 | 0 | 0 |
| 480 | 2 | 2 | 2 | 2 | 0 | 0 |

[1]Japanese Laid-open Patent Application No. 141067/1992

TABLE 14

| Fe/Lf molar ratio | Second invention | | | | | | | | | |
|---|---|---|---|---|---|---|---|---|---|---|
| | pH | | | | | | | | | |
| | 2.0 | 2.1 | 2.5 | 3.0 | 4.0 | 5.0 | 6.0 | 7.0 | 8.8 | 9.0 | 9.2 |
| 10 | 2 | 2 | 2 | 2 | 2 | 1 | 1 | 1 | 2 | 2 | 2 |
| 15 | 2 | 1 | 0 | 0 | 0 | 0 | 0 | 0 | 0 | 0 | 2 |
| 30 | 2 | 1 | 0 | 0 | 0 | 0 | 0 | 0 | 0 | 0 | 2 |
| 60 | 2 | 0 | 0 | 0 | 0 | 0 | 0 | 0 | 0 | 0 | 2 |
| 120 | 2 | 0 | 0 | 0 | 0 | 0 | 0 | 0 | 0 | 0 | 2 |
| 240 | 2 | 0 | 0 | 0 | 0 | 0 | 0 | 0 | 0 | 0 | 2 |
| 480 | 2 | 0 | 0 | 0 | 0 | 0 | 0 | 0 | 0 | 0 | 2 |
| 1000 | 2 | 1 | 1 | 1 | 1 | 0 | 0 | 0 | 0 | 0 | 2 |
| 1200 | 2 | 2 | 2 | 2 | 2 | 2 | 2 | 2 | 2 | 2 | 2 |

As shown above, the iron-Lf complex of the second invention exhibited high storage stability at ordinary temperature in the range of pH 2.1–9.0 even by heating at 90° C. for 10 min. However, the iron-Lf complex of the first invention prepared only by the conditions of 150 molecules or over of iron and one molecule of Lf at pH 6.5 lacked stability. In addition, iron-Lf complex prepared according to the method disclosed in Japanese Laid-open Patent Application No. 141067/1992 lacked heat resistance at pH 6.5 and 7.3 and naturally has no storage stability.

There is no particular restriction for producing products containing Lf complexes of the present invention.

Sterilization is performed by the conventional methods including thermal pasteurization or sterilization. Thermal treatment is performed by low temperature heating at 65° C. for 30 min., or 120° C. for 2–3 sec. or 140°–150° C. for 3–5 sec., or by retort treatment.

Evaporation may provides powder preparations containing heat resistant Lf-iron complexes. Lyophilization can also be applied to give dried products, however low cost spray drying is preferable for the preparation of a large amount of products. Products prepared for dissolution, may be mixed with skim milk, whey, casein, gelatin, sucrose and starch to improve solubility.

The resultant Lf containing products made from Lf complexes contain iron and are particularly suitable for the preparation of foods, feeds and medicines for the prevention and treatment of anemia. The complexes are completely devoid of astringent taste and can be used as iron supplies for iron enriched foods and medicines for oral administration. Furthermore, the products prevent the acceleration of peroxide formation of iron and may be used as iron supplies with easily oxidizable foods, such as fat.

The following test experiment shows the results of gustatory tests.

Test experiment 12

Various iron and Lf complexes prepared by the three methods were desalted and condensed with an ultrafiltration membrane with 5,000 molecular weight cut as those of Test experiment 9, adjusted with the sham buffer, pH 6.8, and diluted with distilled water to give iron concentration of 13 mg and 26 mg/100 ml. The resulting samples were gustatory tested as follows:

Samples were tested by five male and female panelists each on astringent taste using the sham buffer as a control. Panelists were blindfolded not to be impressed by the appearance. Control and one sample were tasted successively and at least one day interval was made prior to the next test. Samples were randomly tasted by each panelist to prevent daily deviations. Number of panelist who sensed astringent taste in 10 panelists are shown in Table 15.

TABLE 15

| Fe/Lf molar ratio | Lf complex (iron concentration: mg/100 ml) | | | | | |
|---|---|---|---|---|---|---|
| | Prior art[1] | | First invention | | Second invention | |
| | 13 | 26 | 13 | 26 | 13 | 26 |
| 15 | 10 | 10 | 0 | 0 | 0 | 0 |
| 30 | 10 | 10 | 0 | 0 | 0 | 0 |
| 60 | 10 | 10 | 0 | 0 | 0 | 0 |
| 150 | 10 | 10 | 0 | 3 | 0 | 0 |
| 240 | 10 | 10 | 1 | 4 | 0 | 0 |
| 480 | 10 | 10 | 1 | 6 | 0 | 0 |

[1] Japanese Laid-open Patent Application No. 141067/1992

As shown above, no astringent taste was felt in the Lf complex, particularly by the second invention of the present invention exhibiting an excellent masking effect. The Lf complexes of the first invention, iron concentrations of 26 mg/100 ml and Fe/Lf molar ratio of 150 or over showed astringent taste in some panelists, and all 10 panelists felt astringent taste even at the lowest concentration and molar ratio in those of the prior art.

Test experiment 13

Various molar ratios of iron and Lf complexes were prepared, desalted and condensed with an ultrafiltration membrane with 5,000 molecular weight cut as those of Test experiment 10. The obtained solutions were diluted with the sham buffer to give iron concentration of 26 mg/100 ml and pasteurized at 90° C. for 10 min. The resulting samples were tested as those of Test experiment 12.

TABLE 16

| Fe/Lf molar ratio | pH | | | | | | | | | |
|---|---|---|---|---|---|---|---|---|---|---|
| | 2.0 | 2.1 | 2.5 | 3.0 | 4.0 | 5.0 | 6.0 | 7.0 | 8.8 | 9.0 | 9.2 |
| 10 | 10 | 9 | 8 | 8 | 7 | 8 | 8 | 5 | 6 | 8 | 10 |
| 15 | 10 | 3 | 2 | 2 | 1 | 0 | 0 | 0 | 0 | 1 | 10 |
| 30 | 10 | 1 | 0 | 0 | 0 | 0 | 0 | 0 | 0 | 0 | 10 |
| 60 | 10 | 0 | 0 | 0 | 0 | 0 | 0 | 0 | 0 | 0 | 10 |
| 120 | 10 | 0 | 0 | 0 | 0 | 0 | 0 | 0 | 0 | 0 | 10 |
| 240 | 10 | 0 | 0 | 0 | 0 | 0 | 0 | 0 | 0 | 0 | 10 |
| 480 | 10 | 2 | 1 | 1 | 1 | 1 | 0 | 0 | 0 | 0 | 10 |
| 1000 | 10 | 3 | 2 | 2 | 2 | 1 | 0 | 0 | 0 | 0 | 2 |

As shown above, the iron-Lf complexes of the second invention of the present application suppressed the astringent taste of iron when 15–1,000 molecules of iron bind with one molecule of Lf and at pH 2.1–9.0. A few panelists sensed some astringent taste when 480 or over molecules of iron bind with one molecule of Lf and at pH range of 2.1–5.0. However, no astringent taste was felt when iron content was made 13 mg/100 ml.

The best mode for practicing the present invention.

The present invention will be explained more in detail by the following examples.

EXAMPLE 1

In eight L of water, 100 g of Lf and 72.4 g of iron nitrate·9$H_2O$ were dissolved and added with five g of $NaHCO_3$ under vigorous stirring to adjust to pH 6.4. Water was added to the mixture to make 10 L in total volume to give a heat resistant iron-Lf complex solution containing 10 g/L of Lf, 100 mg/g Lf of iron ion and 107 mg/g Lf of hydrogencarbonic acid ion.

Half amount of the solution, five L, was lyophilized to give 5.3 g of powder. In a column having two cm of inner diameter and 50 cm of height, Sephadex G-25 (Pharmacia Biotech K.K.) equilibrated with 100 ml of a water was filled in and one ml of the above solution was loaded on the column. The column was eluted with water and Lf in the void volume fractions was collected and determined with Protein Assay kit (Bio-Rad Co., Ltd.) for Lf and ICP for iron. The void fractions contained 9.7 mg of Lf and 1.03 mg of iron ion, which means binding of 106 mg of iron to one g of Lf. No Lf or iron was eluted in the other fractions.

EXAMPLE 2

In 100 ml of water, 0.5 g of Lf and 0.4 g of $FeCl_3·6H_2O$ were dissolved and added with 1M $NaHCO_3$ solution under vigorous stirring to adjust pH 3.5. Additionally, 1N-NaOH was added to make pH 6.2 to give a heat resistant iron-Lf complex solution.

Separately, two kg of skim milk powder was dissolved in 20 L of water and adjusted to pH 6.5 by an addition of a small amount of lactic acid. The prepared reconstituted skim milk was mixed with 100 ml of the prepared heat resistant iron-Lf complex, homogenized, pasteurized at 120° C. for two sec. with a plate type sterilizer and immediately cooled to 5° C. The cooled products contained 25 mg/L of heat resistant iron-Lf complex and 164 mg/g of total iron with electric conductivity of 6.5 ms/cm at pH 6.5. The resulting product containing the heat resistant iron-Lf complex was kept in a refrigerator for two weeks. A portion of the kept product was centrifuged at 1,200 rpm for 10 min., but no precipitate or iron odor was detected indicating the stable existence of heat resistant iron-Lf complex.

EXAMPLE 3

In 100 L of skim milk, 1.3 L of the heat resistant Lf-iron complex solution prepared by the Example 1 was dissolved, homogenized and pasteurized at 150° C. for four sec., then immediately cooled to 4° C. and aseptically filled 250 ml each in paper containers. The divided product was kept at 37° C. each for three months, centrifuged at 1,200 rpm for 10 min., but no precipitate was observed. Coliform group or standard plate count in the products was negative. Brownish discoloration was presumed due to iron content, but no practical disadvantage was found with very faint brown.

EXAMPLE 4

One L each of solution A containing 1.2 moles of $NaHCO_3$ and 10 μmole of Lf (DMV Japan, Branch of Campina Melkunie BV) and solution B containing 1.5 mmole of $Fe_2(SO_4)_3$ as iron ion were prepared. Solution B was added to solution A to prepare an iron-Lf complex solution. The resulting solution was desalted and condensed with an ultrafiltration membrane with 5,000 molecular weight cut and diluted with the sham buffer, pH 8.9, to give iron concentration of 26 mg/100 ml. The diluted solution was poured in test tubes with screw cap, sealed, heated at 90° C. for 10 min., cooled to room temperature and kept for one month at room temperatures. No precipitate was found with naked eyes. Sensory test was performed in a similar manner with that of Test experiment 11 with 10 panelists, but no panelist sensed astringent taste.

EXAMPLE 5

Solution A: one L solution containing 0.05 mole of $CaCO_3$ and 1.2 mole of $NH_4HCO_3$ was adjusted to pH 7.8 with HCl. Solution B1: 0.2 L solution containing 1.5 mmole of $Fe_3(SO_4)_3$ iron ion, and solution B2: 0.8 L solution containing 10 µmole of highly pure transferrin (apo type, derived from bovine plasma, Wako Pure Chemical Ind. Ltd.) were prepared. Solutions B1 and B2 were mixed and this mixture was added to solution A to give iron bound transferrin. The iron and transferrin mixed solution was desalted and condensed with an ultrafiltration membrane with 5,000 molecular weight of cut, and diluted with the sham buffer, pH 6.8, to give iron concentration of 26 mg/200 ml. The diluted solution was poured in test tubes with screw cap, sealed, heated at 90° C. for 10 min., allowed to cool to room temperature and kept at 37° C. for one month. No precipitate was found with naked eyes. Sensory test was performed in a similar manner with that of Test experiment 12 with 10 panelists, but no panelist sensed astringent taste.

EXAMPLE 6

Solution A: one L solution containing 0.5 mole of $Na_2CO_3$ and 0.7 mole of $KHCO_3$ was adjusted to pH 8.3 with acetic acid. Solution B1: 0.2 L solution containing 1.5 mmole of $Fe(NO_3)_3$ as iron ion, and solution B2: 0.8 L solution containing 10 µmole of crude ovotransferrin (typeIV, derived from egg white, free of iron, Sigma Chemical Co.) were prepared. Solutions B1 and B2 were mixed and this mixture was added to solution A to give iron bound ovotransferrin. The iron and ovotransferrin mixed solution was desalted and condensed with an ultrafiltration membrane with 5,000 molecular weight of cut, and diluted with the sham buffer, pH 6.2, to give iron concentration of 26 mg/200 ml. The diluted solution was poured in test tubes with screw cap, sealed, heated at 90° C. for 10 min., allowed to cool to room temperature and kept at 37° C. for one month. No precipitate was found with naked eyes. Sensory test was performed in a similar manner with that of Test experiment 12 with 10 panelists, but no panelist sensed astringent taste.

EXAMPLE 7

Solution A: eight L solution containing 24 moles of $NaHCO_3$ with precipitates of un-dissolved $NaHCO_3$, solution B1: two L solution containing 20 mmole of $FeCl_3$, and solution B2: eight L solution containing 100 µmole of lactoferrin (Tatua Biologics, a Division of the Tatua Co-operative Dairy Co., Ltd.) were prepared. Solutions B1 and B2 were mixed and this mixture was added to solution A with vigorous stirring to give iron bound lactoferrin. The iron and lactoferrin mixed solution was desalted and condensed to one L with an ultrafiltration membrane with 5,000 molecular weight of cut. The resulting solution was added to 20 L of reconstituted skim milk prepared at a rate of 100 g of skim milk powder in one L of wafer to give iron concentration of 26 mg/200 ml. The mixed solution was pasteurized with a plate type sterilizer at 120° C. for two sec., immediately cooled to 5° C. and kept at 10° C. for two weeks. A part of solution was centrifuged at 3,000 rpm for 10 min., but no precipitate was found. Sensory test was performed in a similar manner with that of Test experiment 12 with 10 panelists using a control sample prepared by pasteurization and storage of reconstituted skim milk in a similar manner, but no panelist sensed astringent taste, abnormal taste or odor.

EXAMPLE 8

In 20 L of raw milk, the iron-lactoferrin mixed solution prepared and condensed in Example 7 was added to give iron concentration of 26 mg/200 ml. The solution was homogenized, pasteurized at 150° C. for four sec., immediately cooled to 4° C., aseptically poured 250 ml each in paper containers, kept at 37° C. for three months and centrifuged. No precipitate was found. Coliform group or standard plate count in the products was negative. Brownish discoloration was presumed to be due to iron content, but no practical disadvantage was found with very faint brown. Sensory test was performed in a similar manner with that of Test experiment 12 with 10 panelists using a control group prepared by pasteurization and storage of raw milk in a similar manner, but no panelist sensed astringent taste, abnormal taste or odor.

EXAMPLE 9

An iron-lactoferrin mixed solution prepared and condensed in Example 7 (test group) or a $FeSO_4$ solution (control group No. 1) was dissolved in a phosphate buffer saline, pH 7.2, containing ascorbic acid and sodium ascorbate at 6.2 mg/100 g as vitamin C. The resulting solutions were pasteurized at 90° C. for 10 min. to give test samples. A control group No. 2 was prepared by pasteurization of a phosphate buffer saline with added vitamin C.

Female 21-day-old Wistar rats (Charles River Japan Inc.) immediately after weaning and body weight of 45–50 g were selected. The selected rats were fed with iron deficient feed (Oriental Yeast Co., Ltd., iron content 0.25 mg/100 g feed) for two weeks to prepare anemia rats with blood hemoglobin content of seven g/100 ml or less. Rats were divided in groups with four rats in one group. Rats were fed further with the iron deficient feed and test sample was given orally by gavage at a rate of one ml/day for six weeks. Six weeks after the final administration, blood was drawn from the tail vein and hemoglobin was determined with an automatic blood counter (TOA Electronics Co., Ltd.). The results are shown in Table 17.

TABLE 17

|  | Hemoglobin content | (Average ± SD) |
|---|---|---|
| Test group | 15.2 ± 1.1 | (g/100 ml) |
| Control group No. 1 | 12.9 ± 0.9 |  |
| Control group No. 2 | 4.8 ± 0.3 |  |

As shown above, the iron-Lf complex of the present invention exhibits anemia treating effect and is superior to an inorganic iron compound, $FeSO_4$.

EXAMPLE 10

An iron-lactoferrin mixed solution prepared and condensed in Example 7 was added to raw milk containing ascorbic acid and sodium ascorbate at 30 mg/200 ml as vitamin C to make iron concentration of 15 mg/200 ml. The resulting solution was poured in heat-resisting glass bottles of approximately 200 ml volume to make 10 ml or less of head space (Test group). Vitamin C enriched milk was prepared by addition of sodium iron citrate instead of iron-Lf (Control group). The resultant groups were sterilized at F=four using a retort, kept at 37° C. for two weeks and the residual vitamin C was determined with a vitamin C determination apparatus (TOA Electronics Co., Ltd.) The residual rate (%) was calculated by dividing the determined value with the initial value. The results are shown in Table 18.

TABLE 18

| | Residual rate |
|---|---|
| Test group | 89% |
| Control group | 62% |

As shown above, the iron-Lf complex of the present invention showed less degradation of vitamin C than that of inorganic iron indicating the complex is useful as an effective iron supply with less formation of oxidized products and peroxides.

Furthermore, a sensory test was performed in a similar manner with that of Test experiment 12 with 10 panelists using a control group prepared by retort treatment of vitamin C enriched milk without addition of iron, but no panelist sensed astringent taste, abnormal taste or odor.

EXAMPLE 11

In an 0.2 mole/L acetate buffer, pH 4, one g of Lf (DMV Japan) was dissolved, added with 26,000 unit of pepsin (Sigma Chemical Co.) and incubated at 37° C. for two hrs., then was adjusted to pH 7.5 with NaOH. The resulting solution was mixed with 200,000 unit of trypsin (Sigma Chemical Co.) and incubated at 37° C. for two hrs. An electrophoresis of the obtained degraded Lf confirmed the molecular weight of degradation products of 50 kDa, 40 kDa and 30 kDa.

Solution A: one L solution containing 1.3 moles o f $NaHCO_3$ with precipitates of undissolved $NaHCO_3$, solution B1: 0.2 L solution containing 1.2 mmole of $FeCl_3$ as an iron ion, and solution B2: 0.8 L solution containing degraded lactoferrin which corresponds to 10 μmole of intact lactoferrin were prepared. Solutions B1 and B2 were mixed and added to solution A with stirring to give an iron bound degraded lactoferrin. The resulting solution was poured in test tubes with screw cap, sealed, heated at 90° C. for 10 min., allowed to cool to room temperature and kept at 37° C. for one month. No precipitate was found with naked eyes. Sensory test was performed in a similar manner with that of Test experiment 12 with 10 panelists, but no panelist sensed astringent taste.

Usefulness in industry

The iron-Lf bound compounds, complexes, of the present invention contain large amount of iron and are thermally stable. Thus the complexes can provide physiological activity of lactoferrin and iron to foods and drinks processed by heat treatment.

Furthermore, the complexes show no iron specific astringent taste and prevent the accelerated peroxide formation and are useful for prevention and treatment of anemia, iron enrichment, or prevention of contamination of foods, medicines, feeds and cosmetics with pathogenic microorganisms.

We claim:

1. A heat resistant carbonate or hydrogencarbonate-iron-lactoferrin complex having one molecule of lactoferrin bound with about 15 to about 1,000 molecules of iron via carbonic or hydrogencarbonic acid.

2. A heat resistant carbonate or hydrogencarbonate-iron-lactoferrin complex having one molecule of lactoferrin bound with about 15 to about 1,000 molecules of iron and with about 15 to about 2,000 molecules of carbonic acid or hydrogencarbonic acid.

3. The complex of claim 1 or 2, wherein the lactoferrin is selected from the group consisting of mammalian lactoferrins, transferrin isolated from blood, transfertin isolated from viscera, ovotransferrin, and lactoferrin genetically engineered by microorganisms, animal cells and transgenic animal, in their crude, hydrolyzed by enzyme or pure form.

4. A process for the preparation of heat resistant carbonate or hydrogencarbonate-iron-lactoferrin complexes comprising the steps of:

mixing an aqueous solution of iron, with an aqueous solution of lactoferrin, thereby forming an iron-lactoferrin solution; and mixing said solution with an aqueous solution of carbonate or hydrogencarbonate ion, thereby forming an aqueous solution of said complexes.

5. A process for the preparation of heat resistant carbonate or hydrogencarbonate-iron-lactoferrin complexes comprising the steps of:

mixing an aqueous solution of lactoferrin, with an aqueous solution of carbonate or hydrogencarbonate ion, thereby forming a carbonate or hydrogencarbonate-lactoferrin solution; and mixing said solution with an aqueous solution of iron, thereby forming an aqueous solution of said complexes.

6. The process of claim 4 or 5 further comprising:

filtering the aqueous solution of said complexes through a membrane with a 5,000 molecular weight cut off, thereby forming a filtrate; diluting said filtrate with a buffer to adjust the pH; and isolating said heat resistant carbonate or hydrogencarbonate-iron-lactoferrin complexes.

7. The process of claim 4 or 5 wherein the ratio of iron/carbonate or hydrogencarbonate/lactoferrin in the complexes is from about 15/15/1 to about 1,000/2,000/1.

8. The process of claim 4 or 5 wherein the carbonate compound is selected from the group consisting of carbonated water, $NH_4CO_3$, $NaHCO_3$, $KHCO_3$, $Na_2CO_3$, $CaCO_3$, and mixtures thereof.

9. The process of claim 6 wherein the buffer of step 4 is selected from the group consisting of glycine-HCl having a pH ranging from about 2.0 to 3.5, acetic acid having a pH ranging from about 3.5 to 6.0, imidazole-HCl having a pH ranging from about 6.0 to 7.8 and boric acid-KCl-NaOH having a pH ranging from about 7.8 to 9.3.

10. The process of claim 6 wherein the isolation step comprises evaporation, lyophilisation, chromatography, or spray drying.

11. A heat resistant carbonate or hydrogencarbonate-iron-lactoferrin complex having about 22 to 562 mg of carbonic acid or hydrogencarbonate or carbonate ion, and about 20 to 500 mg of iron per one gram of lactoferrin.

12. The complex of claim 11, wherein the lactoferrin is selected from the group consisting of mammalian lactoferrins, transferrin isolated from blood, transferrins isolated from viscera, ovotransferrin, and lactoferrin genetically engineered by microorganisms, animal cells and transgenic animal, in their crude, hydrolyzed by enzyme or pure form.

13. The complex of claim 12 prepared by a process comprising the steps of: combining an iron solution having a pH<4 with a lactoferrin solution; and adjusting the pH to 7 by adding a carbonate or hydrogencarbonate compound; wherein the iron/carbonate or iron/hydrogencarbonate ratio is in the range of about 20–500 mg 22–562 mg per 1 g of lactoferrin.

14. The complex of claim 13 wherein the carbonate or hydrogencarbonate compound is selected from the group consisting of carbonated water, $NH_4CO_3$, $NaHCO_3$, $KHCO_3$, $Na_2CO_3$, $CaCO_3$, and their mixed solutions.

* * * * *